(12) United States Patent
Seo (10) Patent No.: US 11,129,567 B2
(45) Date of Patent: Sep. 28, 2021

(54) PORTABLE NYSTAGMUS EXAMINATION DEVICE

(71) Applicant: UNIVERSITY INDUSTRY FOUNDATION, YONSEI UNIVERSITY WONJU CAMPUS, Wonju-si (KR)

(72) Inventor: Young Joon Seo, Wonju-si (KR)

(73) Assignee: UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 175 days.

(21) Appl. No.: 15/776,969

(22) PCT Filed: Dec. 27, 2016

(86) PCT No.: PCT/KR2016/015352
§ 371 (c)(1),
(2) Date: May 17, 2018

(87) PCT Pub. No.: WO2017/119659
PCT Pub. Date: Jul. 13, 2017

(65) Prior Publication Data
US 2018/0368763 A1    Dec. 27, 2018

(30) Foreign Application Priority Data
Jan. 4, 2016  (KR) .................. 10-2016-0000506

(51) Int. Cl.
*A61B 3/113*    (2006.01)
*A61B 3/14*    (2006.01)
(Continued)

(52) U.S. Cl.
CPC .............. *A61B 5/4863* (2013.01); *A61B 3/00* (2013.01); *A61B 3/0025* (2013.01);
(Continued)

(58) Field of Classification Search
CPC .......... G02B 27/017; G02B 2027/0187; G02B 27/0172; G02B 27/0093;
(Continued)

(56) References Cited

U.S. PATENT DOCUMENTS

2008/0192202 A1    8/2008  Lewkowski
2011/0317081 A1*  12/2011  Ko ..................... G02B 30/24
                                                  349/13
(Continued)

FOREIGN PATENT DOCUMENTS

CN      104146684 A    11/2014
KR  10-2007-0027541 A   3/2007

*Primary Examiner* — Brandi N Thomas
(74) *Attorney, Agent, or Firm* — Novick, Kim & Lee, PLLC; Jae Youn Kim (57) ABSTRACT

A portable nystagmus examination device includes: a main body which is provided in the form of goggles and comes into contact with the face of a subject so that the visual field of the subject is blocked from the outside; a camera unit which is provided on the inner side of the main body and captures eyeball image information on the subject; a monitor unit which is provided on the outer side of the main body and displays, to a user, the eyeball image information on the subject captured through the camera unit; and a control unit which is provided in the main body, collects the eyeball image information on the subject captured by the camera unit, and controls the monitor unit to output the eyeball image information. Thus, the user can perform the nystagmus examination regardless of a place.

5 Claims, 9 Drawing Sheets

(51) Int. Cl.
*A61B 5/00* (2006.01)
*A61B 3/00* (2006.01)
*A61B 5/11* (2006.01)

(52) U.S. Cl.
CPC .......... *A61B 3/0033* (2013.01); *A61B 3/0041* (2013.01); *A61B 3/113* (2013.01); *A61B 3/14* (2013.01); *A61B 5/00* (2013.01); *A61B 5/0013* (2013.01); *A61B 5/11* (2013.01); *A61B 5/6803* (2013.01); *A61B 2560/0431* (2013.01)

(58) Field of Classification Search
CPC ........ G02B 2027/0138; G02B 27/0176; G02B 2027/0134; G02B 2027/0154; G02B 2027/0169; G02B 2027/0178; G02B 2027/0198; G02B 27/022; G02B 27/028; G02B 27/2228; G02B 7/023; G02B 2027/014; G02B 2027/0141; G02B 27/0101; G02B 2027/0181; G02B 27/00; G02B 27/01; G02B 7/002

See application file for complete search history.

(56) References Cited

U.S. PATENT DOCUMENTS

| | | | |
|---|---|---|---|
| 2013/0083976 A1* | 4/2013 | Ragland | A61B 3/113 382/117 |
| 2014/0320808 A1 | 10/2014 | Kiderman et al. | |
| 2015/0005587 A1* | 1/2015 | Qu | A61B 5/4023 600/301 |

* cited by examiner

PORTABLE NYSTAGMUS EXAMINATION DEVICE

BACKGROUND OF THE INVENTION

Field of the Invention

The present invention relates to a portable nystagmus examination device in which a goggle type main body includes a camera unit capturing eyeballs of a subject and a monitor unit displaying image information captured by the camera unit to a user, and nystagmus examination is possible regardless of a place.

Description of the Related Art

Nystagmus means an unconscious and fast rhythmic movement of eyes. The nystagmus may be caused by a specific condition even in a normal situation and referred to as physiological nystagmus. However, the nystagmus also includes pathological nystagmus which is caused by congenital or acquired lesions of the eyeballs, the nerve, the brain, and the like. Examination of the nystagmus is an important diagnostic means for the clinical examination of organ dysfunction of a patient and many studies on recording, observation, examination, and the like of the nystagmus have been conducted for a long time.

A nystagmus examination device currently used in the medical industry includes goggles worn on the face of a subject, a camera provided in the goggles to capture eyeballs of the subject, and a monitor displaying an eyeball condition of the subject captured by the camera to examine the nystagmus of the subject. A representative example of such a nystagmus examination device is disclosed in the following patent document 1 (hereinafter, referred to as 'the related art'), and a goggle assembly for a video nystagmus recorder according to the related art will be briefly described.

The goggle assembly for the video nystagmus recorder according to the related art includes a hair band coupled to both fixed ends of a main body to fix a flexible main body made of a plastic material and forming an internal space to the head so as to come into contact with the head of a subject to cover both eyeballs; and a video imaging device using a charge-coupled device (CCD) sensor directed toward the eyeballs of a patient on the front surface of the main body to move air ventilation units coupled to a plurality of mounting holes of the main body and the video imaging device in a sliding manner; a mounting frame having a sliding guide rail to be coupled to a sliding groove of the video imaging device; and a frame cover which opens/closes by a hinge coupling portion of the mounting frame in a hinge manner, thereby observing and capturing both eyeballs of the patient by using the single video imaging device.

However, in the goggle assembly for the video nystagmus recorder disclosed in the related art, the video imaging device is slidably coupled to the inside the mounting frame so that both eyeballs can be observed and recorded with only the single video imaging device, and thus, there is an effect to reduce the system components. However, since a video display device is provided separately from the main body, it is inconvenient to perform a nystagmus examination only at a place where the equipment is installed.

Accordingly, it is necessary to develop a nystagmus examination device having both a camera capturing eyeballs of a subject and a monitor displaying an eyeball condition.

SUMMARY OF THE INVENTION

The present invention has been made in an effort to provide a portable nystagmus examination device in which a main body provided in the form of goggles and coming into contact with the face of a subject includes both a camera unit capturing the eyeballs of the subject and a monitor unit displaying eyeball image information of the subject captured by the camera unit, thereby making it possible for a user to perform a nystagmus examination regardless of a place.

Further, the present invention has been made in an effort to provide a portable nystagmus examination device in which the main body includes a sensor unit capable of sensing a posture of the subject and a memory unit recording the eyeball image information, thereby recording both the posture of the subject such as turning of the head of the subject or lowering the upper body and the eyeball image information of the subject acquired by the camera unit.

An exemplary embodiment of the present invention provides a portable nystagmus examination device including: a main body 10 which is provided in the form of goggles and comes into contact with the face of a subject so that the visual field of the subject is blocked from the outside; a camera unit 20 which is provided on the inner side of the main body 10 and captures eyeball image information on the subject; a monitor unit 30 which is provided on the outer side of the main body 10 and displays, to a user, the eyeball image information on the subject captured through the camera unit 20; and a control unit 40 which is provided in the main body 10, collects the eyeball image information on the subject captured by the camera unit 20, and controls the monitor unit 30 to output the eyeball image information.

The portable nystagmus examination device may further include a sensor unit 60 which is provided in the main body 10 and transmits motion information of the subject to the control unit 40 and a memory unit 70 which stores the eyeball image information and the motion information of the subject which are collected by the control unit 40.

The main body 10 may be provided with a wireless communication unit 80 which transmits the eyeball image information and the motion information of the subject collected by the control unit 40 and further include a terminal 90 corresponding to the wireless communication unit 80.

The portable nystagmus examination device may further include a controller 100 transmitting an operation signal to the control unit 40.

A predetermined section of the image captured by the camera unit 20 may be cut based on the sensing result of the sensor unit and the cut image may be stored in the memory unit 70 in correspondence with the motion information of the subject. At the time, a start point of the predetermined section may be a time point when the sensor unit 60 starts to sense the motion of the subject and an end point of the predetermined section may be a time point when the sensor unit 60 completes the sensing of the motion of the subject.

According to the portable nystagmus examination device of the present invention, the camera unit capturing the eyeballs of the subject and the monitor unit displaying the eyeball image information of the subject collected by the camera unit are simultaneously provided, and thus, there is an advantage that the nystagmus examination is possible regardless of a place. Further, the sensor unit collecting the posture information of the subject and the memory unit recording the eyeball image information of the subject of the posture information collected by the camera unit and the sensor unit are further provided, and thus, there is an advantage that the user can confirm the nystagmus state of the subject again after the nystagmus examination.

An additional scope of applicability of the present invention will be apparent from the following detailed description. However, since various changes and modifications within the spirit and scope of the present invention will be apparent to those skilled in the art, it should be understood that the detailed description and specific exemplary embodiments, such as preferred exemplary embodiments of the present invention are just exemplified.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Hereinafter, exemplary embodiments disclosed in the present specification will be described in detail with reference to the accompanying drawings, in which like reference numerals refer to like or similar elements regardless of reference numerals and a duplicated description thereof will be omitted. Further, "module" and "unit" which are suffixes for the components used in the specification are granted or mixed by considering only easiness in preparing the specification and do not have meanings or roles distinguished from each other in themselves. Further, in describing the present invention, when it is determined that the detailed description of the publicly known art related to the present invention may obscure the gist of the present invention, the detailed description thereof will be omitted. Further, the accompanying drawings are only for easily understanding the exemplary embodiment disclosed in the specification and the technical spirit disclosed in the specification is not limited by the accompanying drawings and it should appreciated that the accompanying drawings include all changes, equivalents, or substitutions included in the spirit and the technical scope of the present invention.

A terminal described in the present specification may include mobile terminals, such as mobile phones, smart phones, laptop computers, digital broadcasting terminals, personal digital assistants (PDAs), portable multimedia players (PMPs), navigation systems, slate PCs, tablet PCs, ultrabooks, wearable devices (e.g., a smart watch), smart glasses, head mounted displays (HMD), and the like.

Further, unless a configuration according to an exemplary embodiment disclosed in the present specification can be applied only to mobile terminals, it will be easily understood to those skilled in the art that the configuration may also be applied to fixed terminals such as a digital TV, a desktop computer, and a digital signage.

Figure 1:
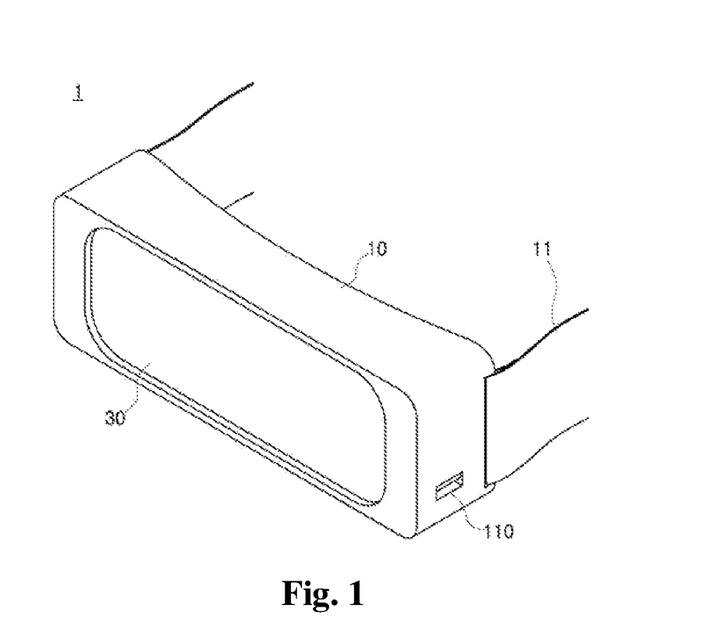
FIG. 1 is a perspective view illustrating a front surface of a portable nystagmus examination device according to the present invention.
Figure 2:
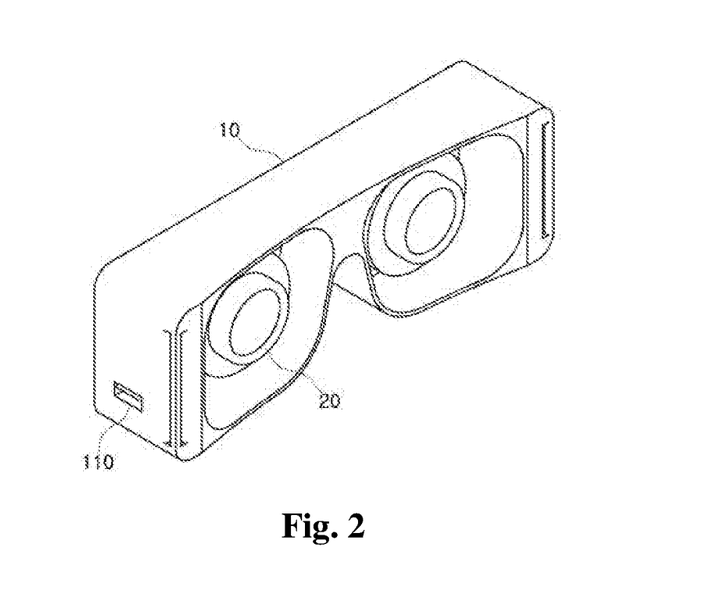
FIG. 2 is a perspective view illustrating a rear surface of the portable nystagmus examination device according to the present invention.
Figure 3:
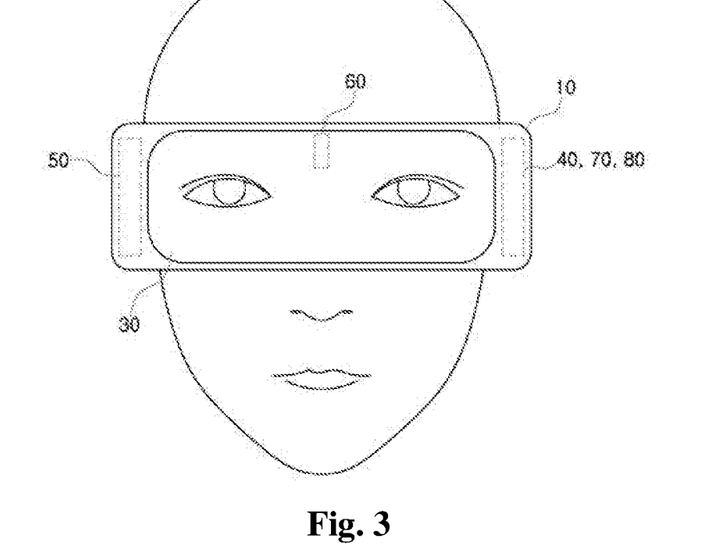
FIG. 3 is a use state view of the portable nystagmus examination device according to the present invention.
Figure 4:
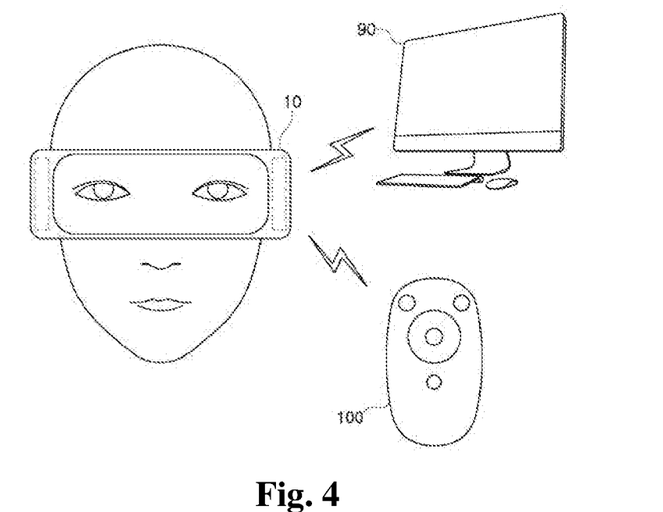
FIG. 4 is a diagram illustrating an exemplary embodiment of the portable nystagmus examination device according to the present invention.
Figure 5:
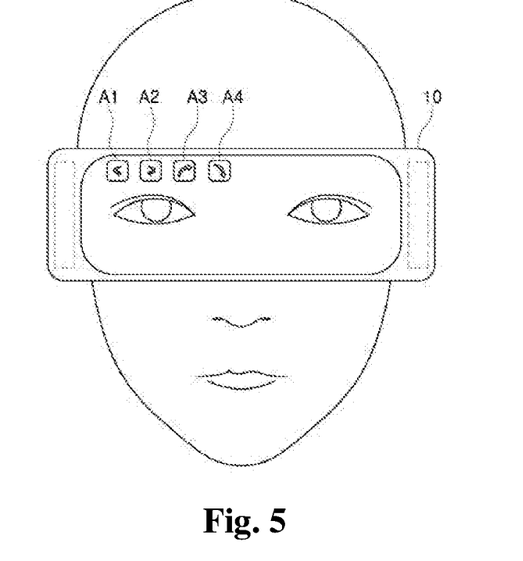
FIG. 5 is a diagram illustrating another exemplary embodiment of the portable nystagmus examination device according to the present invention.
Figure 6:
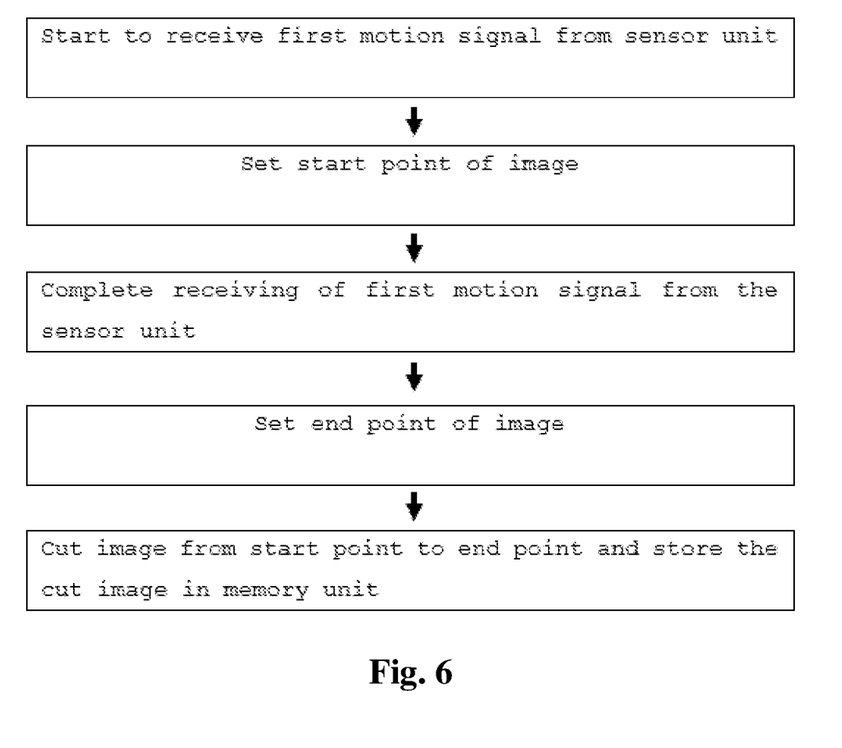
FIG. 6 is a block view illustrating a control order of the portable nystagmus examination device according to the present invention.

First, FIG. 1 is a perspective view illustrating a front surface of a portable nystagmus examination device according to the present invention, FIG. 2 is a perspective view illustrating a rear surface of the portable nystagmus examination device according to the present invention, FIG. 3 is a use state view of the portable nystagmus examination device according to the present invention, FIG. 4 is a diagram illustrating an exemplary embodiment of the portable nystagmus examination device according to the present invention, FIG. 5 is a diagram illustrating another exemplary embodiment of the portable nystagmus examination device according to the present invention, and FIG. 6 is a block view illustrating a control order of the portable nystagmus examination device according to the present invention.

As illustrated in FIGS. 1 to 6, a portable nystagmus examination device includes a main body 10 which is provided in the form of goggles and comes into contact with the face of a subject so that the visual field of the subject is blocked from the outside; a camera unit 20 which is provided on the inner side of the main body 10 and captures eyeball image information on the subject; a monitor unit 30 which is provided on the outer side of the main body 10 and displays, to a user, the eyeball image information on the subject captured through the camera unit; and a control unit 40 which is provided in the main body 10, collects the eyeball image information on the subject captured by the camera unit 20, and controls the monitor unit 30 to output the eyeball image information.

First, the main body 10 will be described in detail. As illustrated in FIG. 2, the main body 10 is worn on the head of the subject and comes into contact with the face of the subject to be fixed to the face so that the visual field of the subject is blocked from the outside.

In this case, the main body 10 includes a frame which is provided in the form of goggles and blocks external light and a sealing attached to the inside of the frame, and the sealing is made of a flexible material such as silicon rubber, epoxy resin, and polyurethane resin and comes into complete contact with the face of the subject so that the visual field is blocked from the outside.

Further, a stretchable hair band 11 such as a rubber band is provided to fix the main body 10 to the head of the subject so that a dynamic examination such as a positional examination may be performed in a nystagmus examination.

Herein, the positional examination is one of methods for examining the nystagmus of the subject and a method of observing the motion of the eyeballs when the head is turned to the left or right or when the subject is laid down and raised. The positional examination is one of methods for the nystagmus examination which are commonly used in medicine and the detailed description will be omitted.

Further, the camera unit 20 is provided on the inner side of the main body 10 at a position corresponding to the eyeball of the subject at the time of being worn. At this time, it is preferred that a pair of camera units 20 is provided in alignment with the eyeballs of the subject and uses a small camera which can capture movement of the eyeballs of the subject in a dark environment. In addition, a camera is provided to simultaneously perform photographing and recording functions and record the eyeball movement of the subject in the form of a photograph or a moving image by an operation of a user.

Further, a pair of monitor units 30 is provided on the outer side of the main body 10 at positions corresponding to the eyeballs of the subject at the time of being worn. In this case, the monitor unit 30 may be provided in size to be received in the frame of the main body 10 and provided so that the eyes of the subject are viewed at a normal position or in a forward direction at a position viewed by the user.

In addition, the monitor unit 30 may be provided to enlarge or reduce eyeball image information of the subject acquired by the camera unit 20 according to the operation of the user. Further, the enlarging or reducing function of the monitor unit 30 may be performed so that left and right monitor units 30 separately operate.

In addition, the monitor unit 30 may be provided as a touch screen so that the user directly touches the monitor unit 30 to perform a series of operations.

Further, a power supply unit 50 is provided in the main body 10 to apply the power to respective components such as the camera unit 20 and the monitor unit 30 which are provided in the main body 10 under a control of the control unit 40.

At this time, the power supply unit 50 may include a battery which is embedded in the main body 10 or detachable from the outside of the main body 10. In addition, the battery includes a connector in the main body 10 and may also be configured to receive the power through a separate power cable or be wirelessly chargeable through a wireless charger. The wireless charging may be implemented by a magnetic induction method or a resonance method (magnetic resonance method).

Meanwhile, the main body 10 includes a sensor unit 60 which transmits motion information of the subject to the control unit 40 and a memory unit 70 which stores the eyeball image information and the motion information of the subject which are collected by the control unit 40.

Herein, the sensor unit 60 is provided in the main body 10 and may include one or more sensors for sensing at least one of information in the portable nystagmus examination device 1 or ambient environment information surrounding the portable nystagmus examination device 1 and subject information.

For example, the sensor unit 60 may include at least one of a gravity sensor, an angular velocity sensor, and a gyroscope sensor. In addition, the portable nystagmus examination device 10 described in the present specification may combine and use information sensed by at least two sensors of the sensors. As a result, the sensor unit 60 senses the posture or movement of the subject in the aforementioned positional examination to transmit the sensed posture or movement to the control unit 40.

Further, the sensor unit 60 may be embedded in the main body 10 and provided between a pair of camera units to more accurately recognize a subject's head turning or bowing motion.

Further, the memory unit 70 is embedded in the main body 10. Further, the memory unit 70 may store programs for the operation of the control unit 40 and include at least one type storage medium of a flash memory type, a hard disk type, a solid state disk (SSD) type, a silicon disk drive (SDD) type, a multimedia card micro type, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

Meanwhile, a predetermined section of the image captured by the camera unit 20 is cut based on the sensing result of the sensor unit 60 under the control of the control unit 40, and the cut image is stored in the memory unit 70 in correspondence with the motion information of the subject sensed by the sensor unit 60.

In particular, a start point of the predetermined section is a time point when the sensor unit 60 starts to sense the motion of the subject and an end point of the predetermined section is a time point when the sensor unit 60 completes the sensing of the motion of the subject. Herein, the positional examination is classified into a first motion of turning the head to the left while the subject is lying, a second motion of turning the head to the right, a third motion of lying back while the subject is sitting, and a fourth motion of backing the head while the subject is lying. The positional examination further includes motions other than the aforementioned motions, but in the present specification, for convenience of the description, only four motions are disclosed, and the motions will be variously modified, added or excluded. For performing the nystagmus examination, when the subject turns the head, rotation angles of about 90° to the left and about 90° to the right are required.

Figure 7:
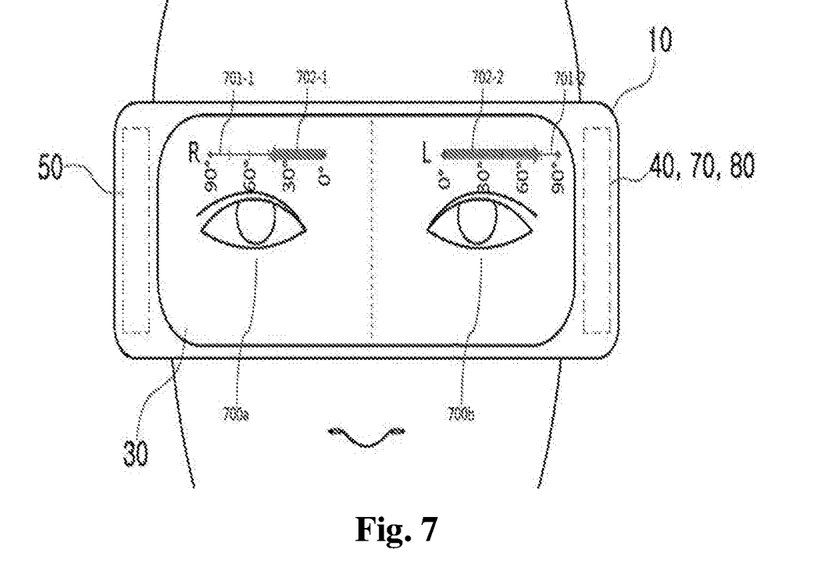
FIGS. 7 and 8 are diagrams illustrating examples of indicators 701-1, 701-2, and 702-1 and 702-2 indicating the degree of rotation of each motion in the nystagmus examination according to an exemplary embodiment of the present invention.
Figure 8A:
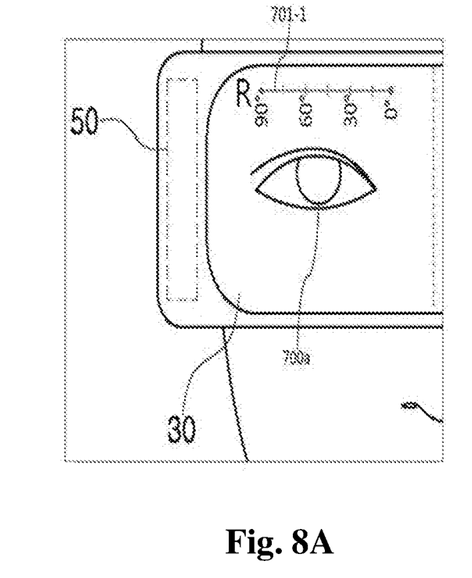
Figure 8B:
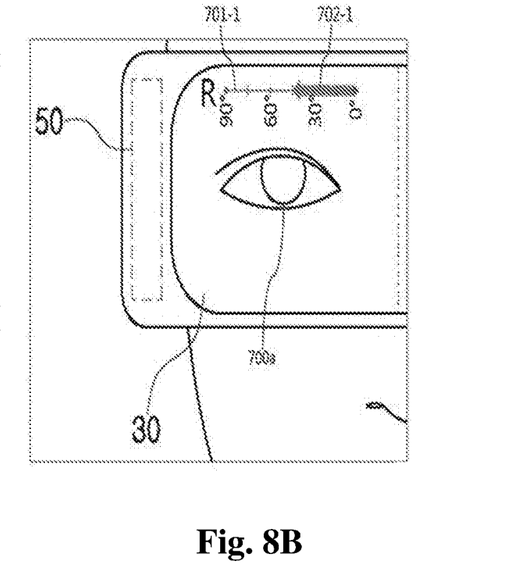

FIGS. 7 and 8 are diagrams illustrating examples of indicators 701-1, 701-2, 702-1 and 702-2 indicating the degree of rotation of each motion in the nystagmus examination according to an exemplary embodiment of the present invention.

As described above, in the nystagmus examination, the subject rotates the head at about 90° to the left/right while lying on the floor or bed. At this time, when the rotation is not secured at a predetermined angle or more, the nystagmus examination may be inaccurate. Accordingly, in the exemplary embodiment of the present invention, it is proposed that indicators for indicating whether the rotation is accurately performed at the predetermined angle or more are further displayed on the monitor unit 30.

According to the exemplary embodiment illustrated in FIG. 7, the control unit 40 displays, on the monitor unit 30, a first rotation indicator 701-1 indicating an angle of turning to the right and a second rotation indicator 701-2 indicating an angle of turning to the left.

The first and second rotation indicators 701-1 and 701-2 may have a range of 0° to 90° and display gradations at predetermined angle intervals (for example, at intervals of 15°). When the head of the subject is rotated to the right (from a state (a) to a state (b) in FIG. 8), a first rotation recording bar 702-1 indicating the rotated angle on the output first rotation indicator 701-1 may be output. In this case, the rotating angle while the head of the subject is rotated will be output by the first rotation recording bar 702-1 in real time. Meanwhile, even though the head is rotated to the right and then returned to the front again, the first rotation recording bar 702-1 may indicate the most rotated angle state while kept as it is.

Similarly, when the head of the subject is rotated to the left, a second rotation recording bar 702-2 indicating the rotated angle may be output on the output second rotation indicator 701-2.

That is, the first and second rotation indicators 701-1 and 701-2 may be indicators for indicating a maximum rotating angle of the head of the subject in the nystagmus examination. According to the example illustrated in FIG. 7, the user verifies the first and second rotation indicators 701-1 and 701-2 to verify (recognize) that the subject rotates only at 45° to the right and rotates only at 75° to the left. Accordingly, the user recognizes an insufficient rotation angle of the subject and guides the subject to completely rotate up to 90° to perform the correct nystagmus examination.

First, as illustrated in FIG. 6, when the first motion is performed after the main body 10 is fixed to the face of the subject, the sensor unit 60 senses a motion of turning the head of the subject to the left and transmits the sensed motion to the control unit 40. Herein, the control unit 40 sets the start point of the predetermined section based on the first motion information of the subject received by the sensor unit 60. Subsequently, when the sensor unit 60 completes the first motion sensing of the subject, the control unit 40 sets the end point of the predetermined section and cuts the eyeball image information of the subject corresponding to the start point and the end point of the predetermined section to store the cut eyeball image information in the memory unit 70 as a separate image.

Further, when the subject performs the second motion, the sensor unit 60 senses a motion of turning the upper body and the head of the subject to the right and transmits the sensed motion to the control unit 40. Herein, the control unit 40 sets a start point of the predetermined section based on the second motion information of the subject received by the sensor unit 60. Subsequently, when the sensor unit 60 completes the second motion sensing of the subject, the control unit 40 sets the end point of the predetermined section and cuts the eyeball image information of the subject corresponding to the start point and the end point of the predetermined section to store the cut eyeball image information in the memory unit 70 as a separate image.

Further, even when the subject performs the third motion or the fourth motion required for the nystagmus examination, the third motion or the fourth motion is stored in the memory unit 70 as a separate image in the same process as the first motion and the second motion. The third motion may be a motion in which the subject lies down while sitting on the bed (accordingly, the head of the subject is rotated at about 90° in the back of the head). In addition, the fourth motion may be a motion (about 60°) of backing the head in a lying state after the third motion.

At this time, as illustrated in FIG. 5, when the eyeball image information of the subject on the first motion to the fourth motion is stored in the memory unit 70 as a separate image, a first motion icon A1, a second motion icon A2, a third motion icon A3, and a fourth motion icon A4 are generated according to each motion in the monitor unit 30. The icons A1, A2, A3, and A4 are represented as the same number as the number of images which are cut in predetermined sections and separately stored in correspondence with the first motion to the fourth motion and the shape of the icon may be provided as a shape meaning the motion information of the subject sensed by the sensor unit 60. A series of processes in which images are separately stored in correspondence with the aforementioned motions of the subject will be summarized in the following Table.

TABLE 1

| Classification | Motion of subject | Process of control unit |
| --- | --- | --- |
| First motion | Turning the head to the left | An image corresponding to the start and the end of the first motion is cut, stored in the memory unit 70, and represented by the first icon A1 on the monitor unit 30. |

TABLE 1-continued

| Classification | Motion of subject | Process of control unit |
| --- | --- | --- |
| Second motion | Turning the head to the right | An image corresponding to the start and the end of the second motion is cut, stored in the memory unit 70, and represented by the second icon A2 on the monitor unit 30. |
| Third motion | Lying in a sitting state | An image corresponding to the start and the end of the third motion is cut, stored in the memory unit 70, and represented by the third icon A3 on the monitor unit 30. |
| Fourth motion | Backing the head in a lying state | An image corresponding to the start and the end of the fourth motion is cut, stored in the memory unit 70, and represented by the fourth icon A4 on the monitor unit 30. |

In addition, when the monitor unit 30 is provided as a touch screen, if the icons A1, A2, A3, and A4 displayed on the monitor unit 30 are pressed, the eyeball image information corresponding to the motion information corresponding to the shape of the icon may be reproduced. At this time, it is preferable that the size or the position of the icon is provided so as not to be disturbed when the user observes the eye image information of the subject.

Meanwhile, the main body 10 is provided with a wireless communication unit 80 which transmits the eyeball image information and posture information of the subject collected by the control unit 40 and further includes a terminal 90 corresponding to the wireless communication unit 80. Herein, the wireless communication unit 80 may include at least module which enables wireless communication between the main body 10 and the terminal 90 of the user. Further, the wireless communication unit 80 may include at least one module connecting the main body 10 to at least one network. The wireless communication unit 80 may include at least one of a broadcast receiving module, a mobile communication module, a wireless Internet module, a short-range communication module, and a position information module. In addition, the terminal 90 may include mobile terminals, such as mobile phones, smart phones, laptop computers, digital broadcasting terminals, personal digital assistants (PDAs), portable multimedia players (PMPs), navigation systems, slate PCs, tablet PCs, ultrabooks, wearable devices (e.g., a smart watch), smart glasses, and head mounted displays (HMD), fixed terminals such as digital TVs, desktop computers, and digital signages, and the like.

In addition, in the exemplary embodiment of the present invention, it is proposed to output an image through a screen of a smart phone in real time by interlocking with an executable application installed in the smart phone. At this time, data may be exchanged through a short-range wireless communication using a smart phone and Bluetooth or Wi-Fi. When a user (for example, a medical professional) rotates the head of the subject to the left or right after the subject (patient) is laid on the bed or floor, the eyes of the subject captured through a smart phone application paired with the nystagmus examination device may be outputted.

In addition, a controller 100 for operating the control unit 40 may be further included. Herein, the controller 100 may be provided wiredly or wirelessly, and when the controller 100 is connected to the main body 10 in a wireless form, the controller 100 may include at least one module which enables a wireless communication between the controller 100 and the controller 40. In addition, the controller 100 may be provided as a commonly used remote controller, and may be provided to operate a photographing function and a recording function of the camera unit 20, enlarging or reducing and contrast adjusting functions of the monitor unit 30, and a function of transmitting the eyeball image information of the subject to the terminal 90 through the wireless communication unit 80.

Meanwhile, the main body 10 is provided with an interface unit 110 and serves as a channel with various kinds of external devices connected to the main body 10. The main body 10 may perform an appropriate control related with the connected external devices in correspondence with the connection of the external devices to the interface unit 110. Herein, the interface unit 110 serves as a path for communication with all the external devices connected to the main body 10. The interface unit 110 receives data from the external devices, supplies power to transmit each component in the main body 10, or transmits data in the main body 10 to the external devices. For example, the interface unit 110 may include at least one of a wired/wireless headset port, an external charger port, a wired/wireless data port, a memory card port, a port connecting devices with identification modules, an audio input/output (I/O) port, a video input/output (I/O) port, an earphone port, and the like.

As an example, when a USB port is provided in the interface unit 110 and connected with the terminal 90 of the user, the image of the eyeball image information stored in correspondence with the motion information of the subject stored in the memory unit 70 is transmitted to the terminal 90 of the user. At this time, the icon corresponding to the image transmitted to the terminal 90 may be automatically deleted from the monitor 30.

Meanwhile, according to a face shape of the subject, the camera unit 20 positioned in the goggle type main body 10 may not fit the position of the eyes, and in the case of a person having small eyes, sizes of eyes 700a and 700b output through the monitor unit 30 may not be sufficient. Accordingly, in the exemplary embodiment of the present invention, a control method of appropriately controlling and outputting the position or size of eyes which may vary according to the subject will be further proposed.

FIGS. 9 to 13 are diagrams illustrating a control method of controlling a position or a size of eyes according to the exemplary embodiment of the present invention.

Figure 9:
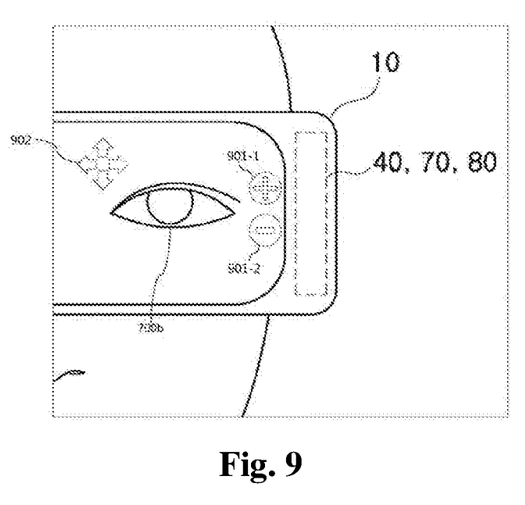
FIGS. 9 to 13 are diagrams illustrating a control method of controlling a position or a size of eyes according to the exemplary embodiment of the present invention.

As illustrated in FIG. 9, the control unit 40 may further output a position adjustment icon 902 and enlargement/reduction icons 901-1 and 901-2 through the monitor unit 30.

Figure 10A:
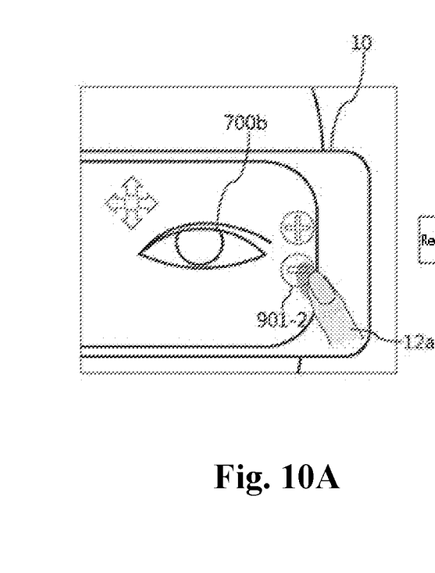
Figure 10B:
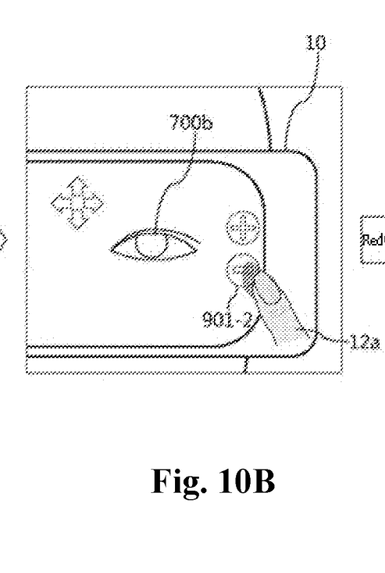
Figure 10C:
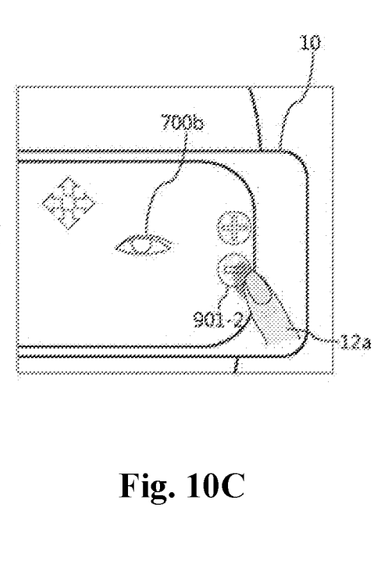
Figure 11A:
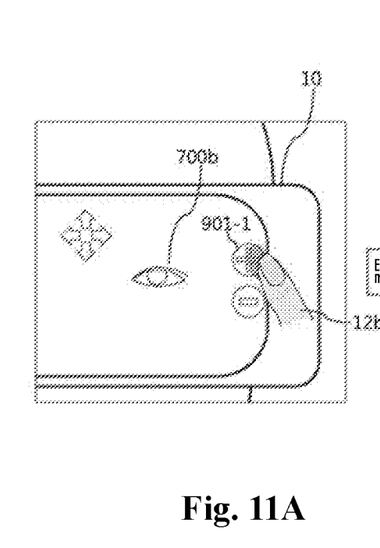
Figure 11B:
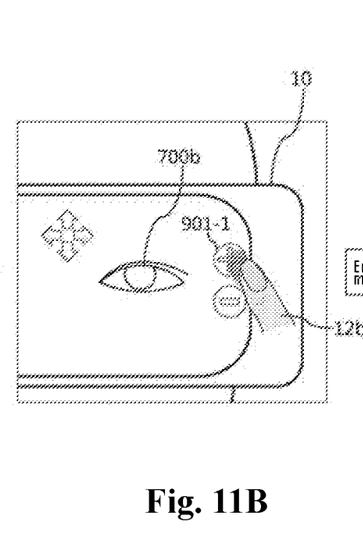
Figure 11C:
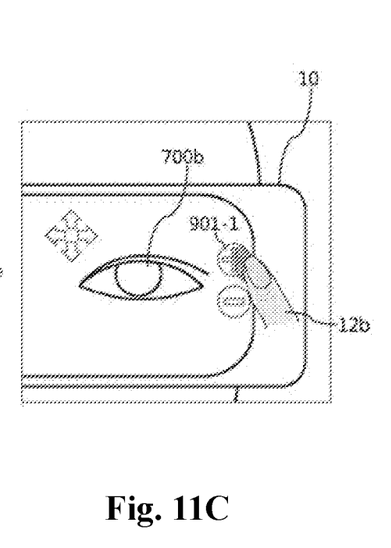
Figure 12:
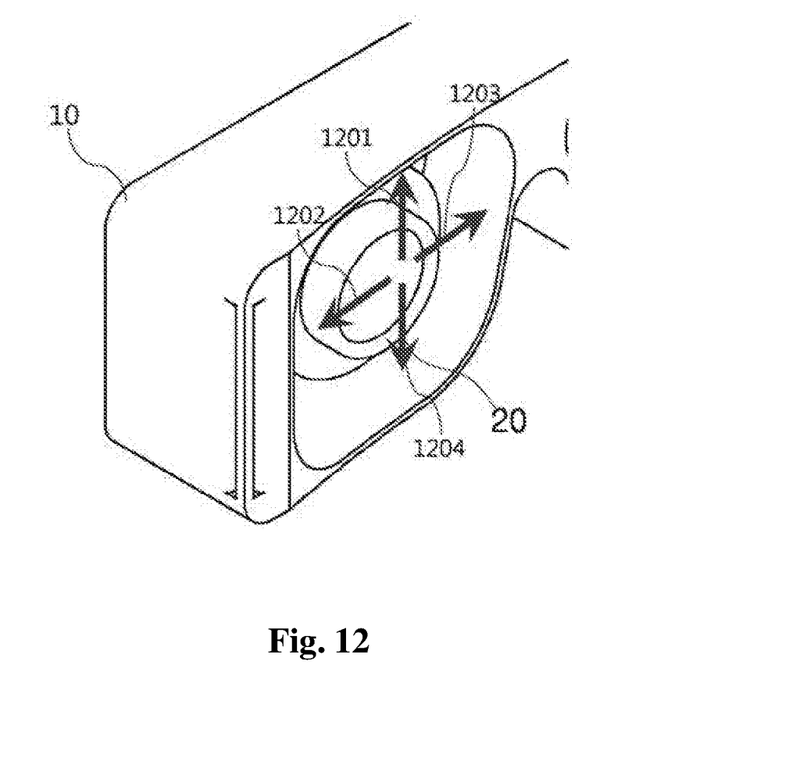

The enlargement/reduction icons 901-1 and 901-2 may mean icons for enlarging/reducing the size of the eyes captured by the camera unit 20. As illustrated in FIG. 10, when an input 12a to which the reduction icon 901-2 is touched is received, the control unit 40 may control the output size of the eyes 700b to be reduced (in order of FIGS. 10A, 10B, and 10C). As illustrated in FIG. 11, when an input 12a to which the enlargement icon 901-1 is touched is received, the control unit 40 may control the output size of the eyes 700b to be enlarged (in order of FIGS. 11A, 11B, and 11C).

The position adjustment icon 902 means an icon for adjusting the upper, lower, left and right positions 1201 to 1204 of the camera unit 20 inside the goggles (see FIG. 12) to exactly match the eye position of the subject. In this case, the nystagmus examination device according to the exemplary embodiment of the present invention may further include a motor (not illustrated) for adjusting the position of the camera unit 20.

Figure 13A:
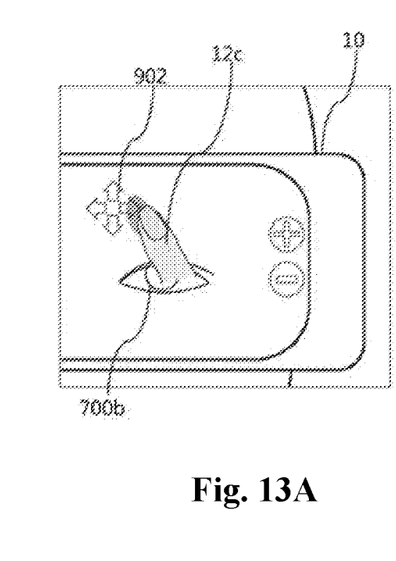
Figure 13B:
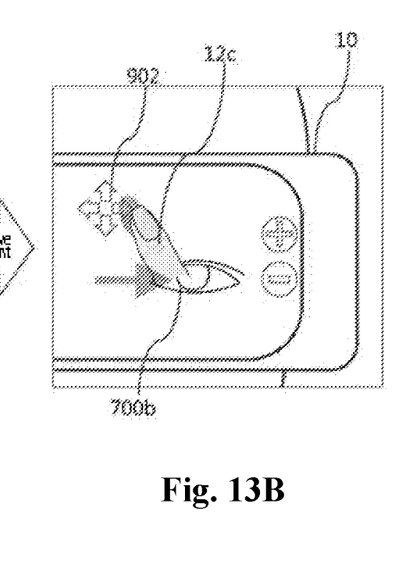
Figure 13C:
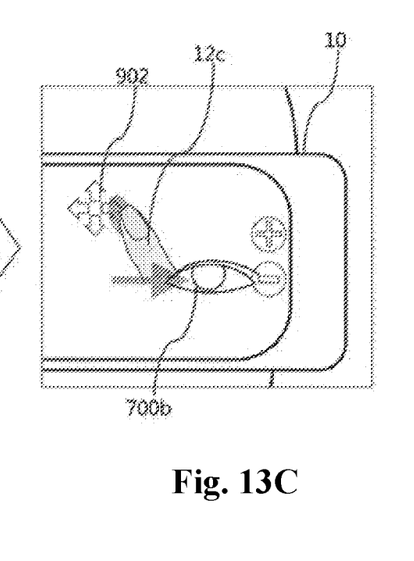

As illustrated in FIG. 13, when an input 12c in which any one of upper, lower, left and right buttons of the position adjustment icon 902 is touched is received, the control unit 40 may control a motor (not illustrated) to move the position of the camera unit 20 in response to the touched button. That is, in an example illustrated in FIG. 13, when the right button is touched 12c, the position of the camera 20 may be adjusted so that the output position of the eyes 700b moves to the right.

Accordingly, through the configurations of the main body 10, the camera unit 20 provided inside the main body 10, and the monitor unit 30 provided outside the main body 10, the user can perform the nystagmus examination of the subject is possible regardless of a place even if a separate monitor device is not provided. Further, through the configuration of the sensor unit 60, the memory unit 70, and the wireless communication unit 80 provided in the main body 10, the nystagmus state of the subject according to the positional examination, and the posture and the motion are recorded and transmitted to the terminal 90 of the user, and thus, there is an advantage that the user can perform the nystagmus examination of the subject again when the user desires.

Although the preferred exemplary embodiments of the present invention have been described in detail, the technical scope of the present invention is not limited to the above-described exemplary embodiments, but should be construed according to the appended claims. It will be understood by those skilled in the art that many modifications and variations are possible without departing from the scope of the present invention.

What is claimed is:

1. A portable nystagmus examination device comprising:
 a main body which is provided in the form of goggles and configured to come into contact with a face of a subject so that a visual field of the subject is blocked from an outside;
 an interface unit which is provided on one side of the main body to receive data from an external device, or transmits data in the main body to the external device;
 a camera unit which is provided on an inner side of the main body and configured to capture eyeball image information on the subject;
 a monitor unit which is provided on the outside of the main body and displays, to a user, the eyeball image information on the subject captured through the camera unit and includes a first rotation indicator indicating an angle of turning to the right of the subject's head and a second rotation indicator indicating an angle of turning to the left of the subject's head; and
 a control unit which is provided in the main body, collects the eyeball image information on the subject captured by the camera unit;
 a sensor unit which is provided in the main body, and configured to transmit motion information of the subject to the control unit; and
 a memory unit for storing the eyeball image information in correspondence with the motion information of the subject collected by the control unit,
 wherein the motion information includes first, second, third and fourth motion information, and the memory units stores the eyeball image information of turning the subject's head left as the first motion information, the eyeball image information of turning the subject's head right as the second motion information, the eyeball image information of the subject lying in a seated state as the third motion information, and the eyeball image information of tilting the subject's head back after lying in the seated state as the fourth motion information, wherein the motion information is displayed on the monitor, and wherein the control unit is configured to display the same number of motion icons as the motion information stored in the memory unit to the user through the monitor unit.

2. The portable nystagmus examination device of claim 1, wherein the main body is provided with a wireless communication unit which transmits the eyeball image information and the motion information of the subject collected by the control unit and further includes a terminal corresponding to the wireless communication unit.

3. The portable nystagmus examination device of claim 1, further comprising: a controller transmitting an operation signal to the control unit.

4. The portable nystagmus examination device of claim 1, wherein a predetermined section of the image captured by the camera unit is cut based on a sensing result of the sensor unit and the cut image is stored in the memory unit in correspondence with the motion information of the subject.

5. The portable nystagmus examination device of claim 4, wherein a start point of the predetermined section is a time point when the sensor unit starts to sense the motion of the subject and an end point of the predetermined section is a time point when the sensor unit completes sensing of the motion of the subject.

\* \* \* \* \*